(12) United States Patent
Chenite et al.

(10) Patent No.: US 8,784,850 B2
(45) Date of Patent: Jul. 22, 2014

(54) HIGHLY BIOCOMPATIBLE DUAL THERMOGELLING CHITOSAN/GLUCOSAMINE SALT COMPOSITION

(71) Applicant: Oligo Médic Inc., Laval (CA)

(72) Inventors: Abdellatif Chenite, Kirkland (CA); Amine Selmani, Montréal (CA)

(*) Notice: Subject to any disclaimer, the term of this patent is extended or adjusted under 35 U.S.C. 154(b) by 0 days.

(21) Appl. No.: 13/908,299

(22) Filed: Jun. 3, 2013

(65) Prior Publication Data

US 2013/0266549 A1    Oct. 10, 2013

Related U.S. Application Data

(62) Division of application No. 13/218,516, filed on Aug. 29, 2011, now Pat. No. 8,506,972.

(60) Provisional application No. 61/377,592, filed on Aug. 27, 2010.

(51) Int. Cl.
*A61K 9/00*  (2006.01)
*A61F 13/00*  (2006.01)

(52) U.S. Cl.
USPC .......................................... 424/400; 424/422

(58) Field of Classification Search
USPC ................................................. 424/400, 422
See application file for complete search history.

(56) References Cited

U.S. PATENT DOCUMENTS 7,148,209 B2 *  12/2006  Hoemann et al. ............... 514/55
2006/0029578 A1    2/2006  Hoemann et al.

FOREIGN PATENT DOCUMENTS

| CA | 2299687 | 2/1999 |
| CA | 2685349 | 5/2001 |
| CA | 2628244 | 5/2007 |

OTHER PUBLICATIONS

Qui et al., "Synergistic interactions during thermosensitive chitosan-β-glycerophosphate hydrogel formation", RSC Advances, 2011, 1: 282-289.
Cho et al., "Effect of urea on solution behavior and heat-induced gelation of chitosan-β-glycerophosphate", Carbohydrate Polymers, 2006, 507-518.
International Search Report of corresponding International application No. PCT/CA2011/000971 dated Nov. 24, 2011.
Liu et al., "Smart gelation of chitosan solution in the presence of NaHCO3 for injectable drug delivery", International Journal of Pharmaceutics, Apr. 28, 2011, 414, pp. 6-15.
Kundu et al., "Development of HAp and B-TCP scaffolds by starch consolidation with foaming method and druf chitosan bilayered based drug delivery system", J Material Sci: Mater Med., Jul. 20, 2010, 21, pp. 2955-2969.
J.-K. Francis Suh, Howard W.T. Matthhew, "Application of chitosan-based polysaccharide biomaterials in cartilage tissue engineering: a review", Biomaterials, 2000, 21: 2589-2598.
Ruel-Gariépy et al., "Characterizaiton of thermosensitive chitosan gels for the sustained delivery of drugs", International Journal of Pharmaceutics, 2000, 203: 89-98.

* cited by examiner

*Primary Examiner* — Michael G Hartley
*Assistant Examiner* — Robert Cabral
(74) *Attorney, Agent, or Firm* — Norton Rose Fulbright Canada

(57) ABSTRACT

The present disclosure relates to a chitosan solution neutralized with amino-sugar carbonate buffering solution or amino-sugar phosphate buffering solution or phosphorylated amino-sugar buffering solution. The resulting thermogelling chitosan composition is highly biocompatible, isotonic and has the ability to rapidly turn into gel upon heating to the body temperature. It provides a novel chitosan-based composition to suitable for drug delivery, cell delivery and repair or regeneration of tissues and organs as well as other clinical treatment.

19 Claims, 2 Drawing Sheets

HIGHLY BIOCOMPATIBLE DUAL THERMOGELLING CHITOSAN/GLUCOSAMINE SALT COMPOSITION

CROSS REFERENCE TO RELATED APPLICATION

This application is a divisional application of U.S. application Ser. No. 13/218,516, filed Aug. 26, 2011, which claims priority from of U.S. Provisional Application Ser. No. 61/377,592, filed Aug. 27, 2010, and U.S. Provisional Application Ser. No. 61/444,646, filed Feb. 18, 2011, the specification of which are hereby incorporated by reference.

TECHNICAL FIELD

The present description relates to chitosan solution neutralized with amino-sugar carbonate buffering solution, amino-sugar phosphate buffering solution or phosphorylated amino-sugar buffering solution.

BACKGROUND ART

Hydrogels are continuously gaining increased attention as biomaterials for biomedical applications, such as tissue engineering and therapeutics delivery. Furthermore, in situ forming hydrogels or those exhibiting the specific ability of increasing their viscosity with temperature, also called thermosensitive, are preferred over preformed hydrogels, since cells and bioactive compounds, such as drugs, may be easily mixed with the precursor solutions prior to gelation to give homogeneously loaded gels. In addition, in situ gelation facilitates the application and allows for minimally invasive surgery and for adequately fill complex shaped lesion cavities.

Chitosan is an amino polysaccharide obtained by partial to substantial alkaline N-deacetylation of chitin also named poly(N-acetyl-D-glucosamine), which is a naturally occurring biopolymer found in exoskeleton of crustaceans, such as shrimp, crab and lobster shells. Chitosan contains free amine ($—NH_2$) groups and may be characterized by the proportion of N-acetyl-D-glucosamine units and D-glucosamine units, which is expressed as the degree of deacetylation (DDA) of the fully acetylated polymer chitin. The properties of chitosan, such as the solubility and the viscosity, are influenced by the degree of deacetylation (DDA), which represents the percentage of deacetylated monomers, and the molecular weight (Mw).

Chitosan has been proposed in various formulations, alone and with other components, to stimulate repair of dermal, corneal and hard tissues in a number of reports (U.S. Pat. Nos. 4,572,906; 4,956,350; 5,894,070; 5,902,798; 6,124,273; and WO 98/22114). The properties of chitosan that are most commonly cited as beneficial for the wound repair process are its biodegradability, adhesiveness, prevention of dehydration and as a barrier to bacterial invasion. The interesting haemostatic potential of chitosan has also led to its direct application to reduce bleeding at grafts and wound sites (U.S. Pat. No. 4,532,134). Some studies claim that the haemostatic activity of chitosan derives solely from its ability to agglutinate red blood cells while others believe its polycationic amine character can activate platelets to release thrombin and initiate the classical coagulation cascade thus leading to its use as a haemostatic in combination with fibrinogen and purified autologous platelets (U.S. Pat. No. 5,773,033).

One technical difficulty that chitosan often presents is a low solubility at physiological pH and ionic strength, thereby limiting its use in a solution state. Thus typically, dissolution of chitosan is achieved via the protonation of amine groups in acidic aqueous solutions having a pH ranging from 3.0 to 5.6. Such chitosan solutions remain soluble up to a pH near 6.2 where neutralisation of the amine groups reduces interchain electrostatic repulsion and allows attractive forces of hydrogen bonding, hydrophobic and van der Waals interactions to cause polymer precipitation at a pH near 6.3 to 6.4. Admixing a polyol-phosphate dibasic salt (i.e. glycerol-phosphate) to an aqueous solution of chitosan can increase the pH of the solution while avoiding precipitation. In the presence of these particular salts, chitosan solutions of substantial concentration (0.5-3%) and high molecular weight (>several hundred kDa) remain liquid, at low or room temperature, for a long period of time with a pH in a physiologically acceptable neutral region between 6.8 and 7.2. This aspect facilitates the mixing of chitosan with cells in a manner that maintains their viability. An additional important property is that such chitosan/polyol-phosphate (C/PP) aqueous solutions solidify or gel when heated to an appropriate temperature that allows the mixed chitosan/cell solutions to be injected into body sites where, for example cartilage nodules can be formed in subcutaneous spaces.

Chitosan is thus recognized as a biodegradable, biocompatible, antibacterial and haemostatic biopolymer that is able to promote wound healing, drug absorption, and tissue reconstruction. Due to the above mentioned intrinsic properties, chitosan also has been widely explored in numerous cosmetic and pharmaceutical applications. Therefore, considering the great potential of chitosan, there is a continuous need to improve the properties of known thermosensitive chitosan hydrogels which are still considered as very promising for a wider range of biomedical applications.

U.S. Pat. No. 6,344,488, discloses a pH-depend temperature controlled chitosan composition prepared by neutralizing a commercial chitosan having a deacetylation degree ranging from 70 to 95% with mono-phosphate dibasic salts of polyols or sugars, phosphorylated polyols or phosphorylated sugars, exemplified in particular with $\beta$-glycerophosphate ($\beta$-GP). Because of its unique properties, the thermogelling chitosan-GP system has raised significant biomedical interest. However, high concentration of $\beta$-GP was required, particularly for chitosan having DDA between 70 and 85%, in order to achieve fast gelation at body temperature and to avoid rapid elimination of the hydrogel after its administration (Chemte et al., 2000, Biomaterials, 21: 2155-2161; and Chemte et al., 2001, Carbohydrate Polymers, 46: 39-47). This resulted into very high osmolarity, more than twice of that of physiological extracellular fluid (Crompton et al., 2007, Biomaterials, 28: 441-449; and Hoemann et al., 2005, Osteoarthritis Cartilage, 13: 318-329). Ideally, the hydrogel should be isotonic with the extracellular fluid; and its osmolarity should be around 300 mOsm. The osmolarity is a very important factor regulating biocompatibility of the hydrogel with cells either in vitro or in vivo.

Further, in an attempt to improve the gelation properties of chitosan-GP system, particularly for isotonic compositions, U.S. patent application publication No. 2009/0202430 proposed the addition of glyoxal as chemical crosslinker. In another description, particular composition of chitosan-GP system has been combined with blood in the attempt to improve and stabilize blood clots (U.S. Pat. No. 7,148,209 and U.S. patent application publication No. 2010/0178355).

U.S. patent applications Nos. 2009/0270514 and 2010/0113618 described the preparation of thermogelling chitosan solutions by using, instead of β-GP, either $(NH_4)_2HPO_4$ solution or NaOH solution respectively. However, the use of ammonium phosphate salts or all the salts derived from organic bases as disclosed in U.S. patent applications No. 2009/0270514 may be harmful or damageable to cells and living tissues, even if they are at a concentration which normally leads to isotonic thermogelling chitosan solutions. U.S. patent applications No. 2010/0113618 was restricted to reacetylated chitosan having a degree of deacetylation (DDA) ranging from 30 to 60%. Moreover, the NaOH solution is beforehand added with high concentration of 1,3-propanediol, an organic reagent which can be potentially toxic to cells and living tissues. Despite the slight improvement provided by the use polyoses or polyols instead 1,3-propanediol, as disclosed in U.S. patent applications No. 2009/0004230, the toxicity problem remain unsolved, so the system can not be a suitable matrix for cells, sensitive proteins or living tissues.

It is also well known that a solution of bicarbonate salt as $NaHCO_3$, a weak base, can be used to increase the pH of chitosan solution in the vicinity of 6.5 without causing any precipitation, but the resulting solution is unable to turn into homogeneous hydrogel in temperature range between 0 and 50° C. In fact, a pseudo-gelation can be observed, occurring at the surface of the solution caused by the release of $CO_2$, as has been reported by recent study (Liu et al., 2011, Int. J. Pharm., 414: 6-15). In such a case, to achieve gelation of the whole sample, it is necessary to disturb the solution and bring ungelled solution to the surface from the bottom of the sample. This leads to non homogeneous hydrogel.

Thus, there is still a need to be provided with an improved thermogelling chitosan solution having better biocompatibility properties, that is not toxic to cells and living tissue.

SUMMARY

In accordance with the present description there is now provided a biocompatible thermogelling composition comprising chitosan; and a buffering solution;

In an embodiment, the composition is liquid at a pH between 6.5 and 7.6 and at a temperature between about 15° C. and about 22° C., and forms a gel when heated up to a temperature range between about 25 and about 60° C.

The composition disclosed herein can also form gels when cooled down to a temperature between about 8° C. and about 1° C., a temperature around 4° C.

It is also provided herein a method of preparing a thermogelling composition of chitosan, comprising the steps of dissolving chitosan in an acidic solution to obtain an aqueous solution of chitosan; and admixing a buffering solution to the aqueous chitosan solution, to obtain the thermogelling composition of chitosan as described herein.

In an embodiment, the temperature is maintained between 15° C. and 22° C. (room temperature range) during the preparation.

In accordance with the present disclosure, it is also provided a method for delivering a material or compound to a subject in need thereof, comprising the steps of admixing the thermogelling composition described herein with the material or compound; and administering the admixed composition and material and/or compound to the subject.

It is also provided a method of treating, repairing, regenerating, replacing or substituting a tissue or organ within a mammalian or human body comprising the step of administering the composition described herein.

It is also provided the use of the composition described herein for treating, repairing, regenerating, replacing or substituting a tissue or organ within a mammalian or human body.

In a preferred embodiment, the buffering solution is an amino-sugar carbonate solution, an amino-sugar phosphate solution or a phosphorylated amino-sugar solution.

In another embodiment, the buffering solution is a glucosamine carbonate solution, a glucosamine phosphate solution or a glucosamine-6-phosphate solution.

The thermogelling composition described herein can have a pH between 6.7 and 7.2.

In another embodiment, the thermogelling composition is in a liquid state at temperature between 15° C. and 22° C.

In a further embodiment, the thermogelling composition turns into gel when heated up to a temperature of 37° C. or cooled down to a temperature around 4° C.

The concentration of chitosan can range from 0.1% to 5.0% or from 1.0% to about 3.0%; the concentration of glucosamine carbonate, glucosamine phosphate or glucosamine-6-phosphate can range from 0.002M to 0.100M.

In a preferred embodiment, the ratio of chitosan to glucosamine carbonate, of chitosan to glucosamine phosphate and/or the ratio of chitosan to glucosamine-6-phosphate is approximately between 1 and 3. There is a direct relationship between this ratio and the pH of the thermogelling composition and the gelation temperatures.

In another embodiment, the chitosan has a degree of deacetylation (DDA) ranging between 70% and 100% and a molecular weight (Mw) ranging from 50 kDa to 1000 kDa; preferably a DDA of 80% to 99%, and a Mw of 200 kDa to 500 kDa.

In another embodiment, the thermogelling composition can further comprise at least one material or compound, such as for example but not limited to cells, stem cells, peptides, growth factors, human blood, platelet-rich plasma, nucleotides, drugs and/or imaging agents.

In another embodiment, the osmolarity of said composition is between 270 mOsmol/kg and 340 mOsmol/kg.

In another embodiment, the composition is injected to a tissue defect in a patient, then gelled in the tissue defect.

In an alternate embodiment, the composition is pregelled before being injected in a tissue defect in a patient.

In a further embodiment, the composition is administered in order to treat, repair, regenerate, replace or substitute, either totally or partially, a tissue or organ within a mammalian or human body.

In another embodiment, the composition is injected intrarticular to treat or improve body joint functions, or to repair cartilage defects.

In another embodiment, the material or compound is calcium phosphate particles at a concentration comprising between 1.0% and 40.0%.

The calcium phosphate particles can be biphasic calcium phosphates, tetra-calcium phosphates, tri-calcium phosphates, hydroxyapatite, di-calcium phosphates, mono-calcium phosphates, amorphous calcium phosphates, octa-calcium phosphate, fluorinated calcium phosphate, strontied calcium phosphate, or a mixture thereof.

Particularly, the biphasic calcium phosphate particles are sized from 50 to 1000 microns.

Further particularly, the biphasic calcium phosphates comprise from 20% to 85% of tri-calcium phosphate; and from 80% to 15% of hydroxyapatite.

In a further embodiment, the composition is injected and administered as an homogeneous gel.

Particularly, the homogeneous gel has a setting time from 1 minute to 30 minutes, and turns into a composite solid scaffold.

BRIEF DESCRIPTION OF THE DRAWINGS

Having thus generally described the nature of the invention, reference will now be made to the accompanying drawings.

DETAILED DESCRIPTION

Figure 1:
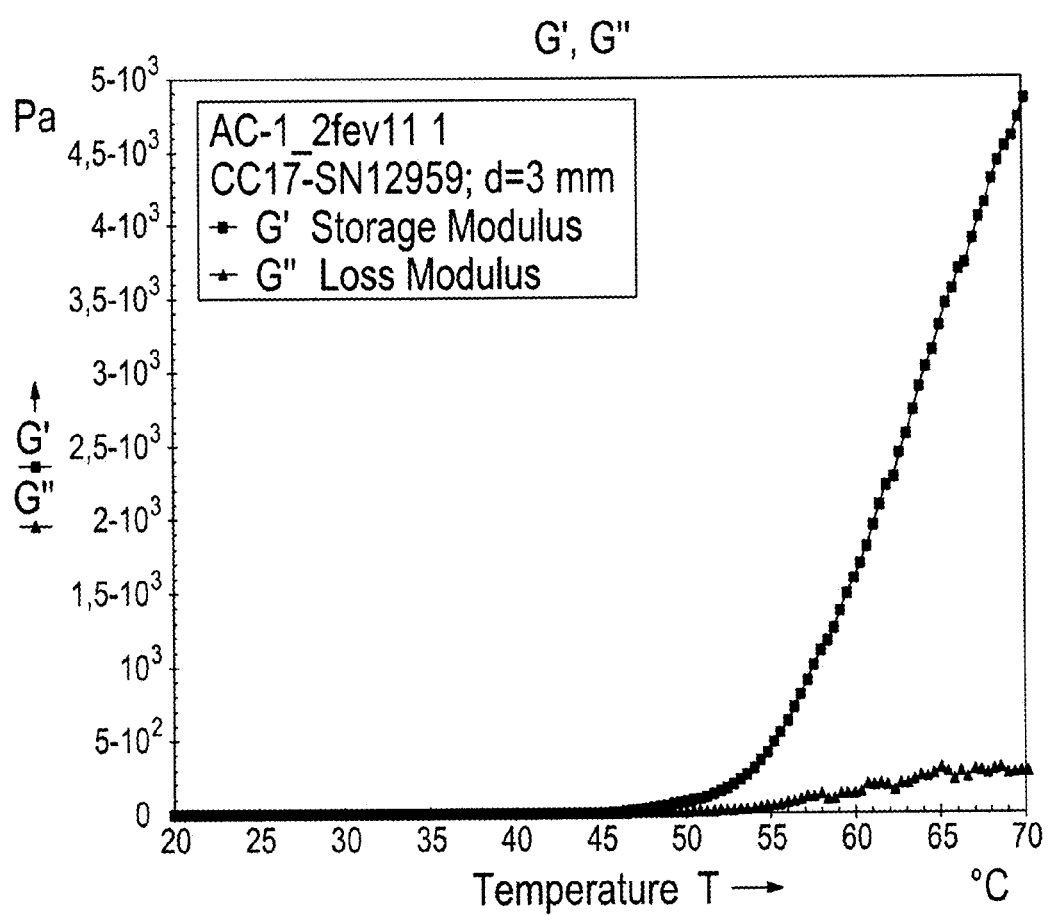
FIG. 1 illustrates the evolution of the elastic modulus and viscous modulus with the temperature of a thermogelling composition having a pH value around 6.7 (chitosan DDA=98%) as described herein.
Figure 2:
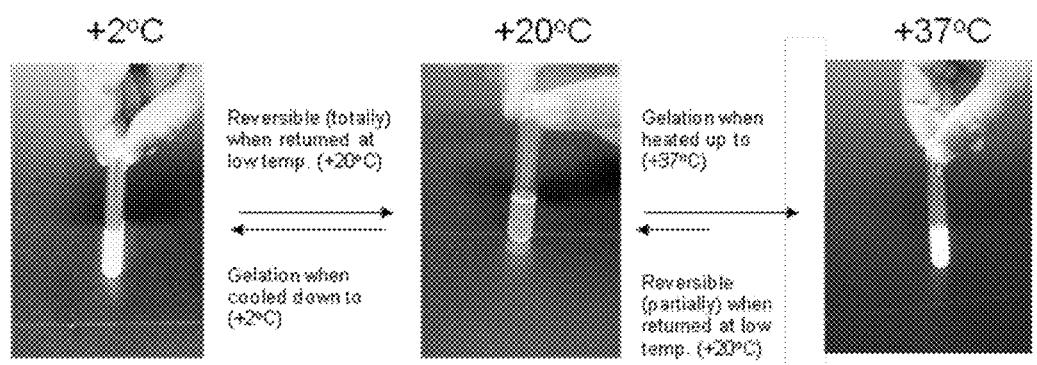
FIG. 2 shows a thermogelling composition as described herein undergoing dual thermogelation. This typical image illustrates dual thermogelation obtained for chitosan solution (DDA=80% or 98%) neutralized either with glucosamine carbonate buffering solution or with glucosamine phosphate buffering solution.

It is provided an aqueous chitosan solution neutralized with amino-sugar carbonate buffering solution, with amino-sugar phosphate buffering solution or with phosphorylated amino-sugar buffering solution. The resulting thermogelling chitosan composition is highly biocompatible, isotonic and has the ability to rapidly turn into gel upon heating to the body temperature. In a preferred embodiment, the chitosan solution is neutralized either with an amino-sugar carbonate buffering solution, with a glucosamine phosphate buffering solution or with a glucosamine-6-phosphate dibasic buffering solution.

The present description discloses the preparation of thermogelling chitosan hydrogels neutralized with a buffering solution of glucosamine carbonate, glucosamine phosphate and/or of glucosamine-6-phosphate. Glucosamine carbonate and glucosamine phosphates are salts where the cation is none other than the positively charged glucosamine, which is the repeating unit in chitosan itself. Either glucosamine or glucosamine-6-phosphate are abundantly found in human tissue and joints, and improve the biocompatibility and bioactivity of the thermogelling chitosan solutions.

The thermogelling chitosan solutions described herein are neutral and highly biocompatible, and can be used in a wide array of biomedical applications as injectable hydrogels for controlled and prolonged delivery of drugs, proteins and growth factors, injectable fillers, injectable composites, as tissue adhesive and wound dressing materials and as scaffolds for tissue engineering applications.

It is described herein the preparation of a chitosan solution, having physiological pH, able to undergo thermogelation upon heating up to around body temperature. In one aspect, the thermogelling or thermosetting chitosan solution is prepared by admixing appropriate amounts of glucosamine carbonate solution or of glucosamine phosphate solution to chitosan solution at room temperature, preferably between 15 and 22° C., under vigorous stirring. The resulting solutions, even at pH between 6.7 and 7.2, have been found to remain liquid at room temperature and turn into hydrogels when heated up to 37° C. or above. The time required for gelling to occur has been found to mainly depend on the temperature and the pH of the final solution, which in turn depend on the amount of glucosamine hydrogen phosphate solution called "buffering solution" and the concentration of chitosan solution. In one aspect, the final pH of an efficient thermogelling chitosan solution should be at least about 6.7. In a separate embodiment, the thermogelling chitosan solutions can also form hydrogels upon cooling to a temperature between 8 and 1° C.

The thermogelling chitosan composition described herein is highly biocompatible with cells, sensitive proteins and living tissues, as glucosamine carbonate or glucosamine phosphate, are used as the buffering solutions, the virtues of glucosamine being conserved. Glucosamine is an amino-sugar naturally synthesized from glucose and glutamine, an amino acid. It is abundant in human joints where it is a key precursor for the biochemical synthesis of various compounds including glycolipids, glycoproteins, glycosaminoglycans, hyaluronate and proteoglycans. All those compounds are present in cartilage and other joint components where they fulfill important roles for joint resilience and lubrication.

With age, the body gradually loses its ability to convert glucose and glutamine into glucosamine, due to lower levels of the converting enzyme glucosamine synthetase. This gradual decrease has been suggested to be one of the main factors contributing to degenerative joint diseases such as osteoarthritis (OA). Clinical group studies and claims by patients support the fact that a daily supplement of glucosamine over a period of time can have beneficial effects for OA patients. Apparently, glucosamine might act to improve cartilage resilience by stimulating in vivo the biosynthesis of glucosaminoglycan.

Exoskeleton of crustaceans, such shrimp, crab and lobster shells are usually the source of commercial glucosamine, which is obtained by the break down or the degradation of chitosan to the monomer unit.

Clinical studies and claims by patients support the fact that a daily supplement of glucosamine over a period of time can have beneficial effects for OA patients. From a safety viewpoint, human studies have consistently reported that the administration of glucosamine did not affect the plasma levels of glucose or insulin, insulin sensitivity or glucose oxidation (Scroggie et al., 2003, Archives of Internal Medicine, 163: 1587-1590; Pouwels et al., 2001, J. Clin. Endocrinol. Metab., 86: 2099-2103; and Monauni et al., 2000, Diabetes, 49: 926-935). This indicates that glucosamine had no significant effect on blood glucose metabolism even in patients with type 2 diabetes mellitus.

Anderson and coworkers reviewed the clinical trial data recorded for more than 3000 patients, and stated that the oral administration of glucosamine was moderately to highly effective in treating osteoarthritis pain, and had no adverse effects on blood, urine or fecal parameters (Anderson et al., 2005, Food and Chemical Toxicology, 43: 187-201). Furthermore, the review summarizes results about very high doses of glucosamine administered orally to rats, mice, rabbits, dogs and horses, as reported in nearly 20 animal studies. The $LD_{50}$ was estimated to exceed 5000 mg/kg for rats and 8000 mg/kg for mice and rabbits. The investigation also showed that the ingestion of glucosamine at high doses, ranging from 300 to 2149 mg/kg of body weight, have no effect on blood glucose levels in rats, rabbits or dogs. Moreover, in fifty-four outpatients with gonarthrosis, a double-blind clinical test was conducted with the aim of evaluating the efficacy and tolerance of intra-articular Glucosamine in comparison with a 0.9% NaCl placebo. Each patient had one intra-articular injection per week for five consecutive weeks. Pain, active and passive mobility of the joint, swelling, and generalized and local intolerance symptoms were recorded before beginning the treatment, and four weeks after the last injection. Glucosamine reduced pain to a significantly greater extent than did placebo, and resulted in significantly more pain-free patients. The angle of joint flexion substantially increased after glucosamine treatment. Active mobility increased with both treatments, with a more favourable trend after glucosamine administration. Knee swelling did not decrease significantly after glucosamine, whereas it worsened (although no significantly) after placebo. There were no local or general intolerance symptoms during and after treatment.

Glucosamine administration was able to accelerate the recovery of arthrosic patients, with no resulting side effects, and to partially restore articular function. In addition, the clinical recovery did not fade after treatment ended, but lasted for the following month, at least. Glucosamine therapy therefore was shown to deserve a selected place in the management of osteoarthrosis (Vajaradul et al., 1981, Clin Ther., 3:336-343). Chitosan has been registered to GRAS (Generally Recognized As Safe). Chitosan composition and materials have been extensively analyzed in vitro as well as in vivo, both in animals and humans. In vitro, chitosan compositions have been tested with various cell lines, including Caco-2 cells, HT29-H, CCRF-CEM (human lymphoblastic leukaemia), and L132 (human embryonic lung cells), MCF7 and COS7 cells (Kean et al., 2010, Advanced Drug Delivery Reviews, 62: 3-11; Richardson et al., 1999, Int. J. Pharm., 178: 231-243; Schipper et al., 1996, Pharm. Res., 13: 1686-1692; Schipper et al., 1999, Eur. J. Pharm. Sci., 8: 335-343; and Zhang, et al., 2008, Biomaterials, 29: 1233-1241).

In vivo, chitosan compositions and materials have been tested in various animal models and through several administration routes. Chitosan has been safely studied in mouse models (immunogenicity), rat models, guinea pig models, and rabbit models (subacute toxicity). No "significant toxic effects" of chitosan were noted in acute toxicity tests in mice, no eye or skin irritation in rabbits and guinea pigs respectively. In the same study it was also concluded that chitosan was not pyrogenic. Exposure of rat nasal mucosa to chitosan solutions at 0.5% (w/v) over 1 h caused no significant changes in mucosal cell morphology compared to control. From most studies reported it appears that chitosan shows minimal toxic effects and this justifies its selection as a safe material in drug delivery. Chitosan/b-Glycerophosphate systems have been investigated in vitro, in vivo in animal models and in humans, and have shown a safe and non-toxic profile (Hirano et al., 1991, Agric. Biol. Chem., 55: 2623-2625; Ono et al., 2000, J. Biomed. Mater. Res., 49: 289-295; Azad et al., 2004, J. Biomed. Mater. Res. B Appl. Biomater., 69: 216-222; Ishihara et al., 2001, Wound Repair Regen., 9: 513-52; and Illum et al., 1994, Pharm. Res., 11: 1186-1189).

In humans, a phase 2 clinical trial involving the percutaneous injection of chitosan-[166]holmium complex, for the treatment of hepatocellular carcinoma, on patients with poor surgical prospects, reported safe and efficacious results. The effects of chitosan have been investigated on eighty patients with renal failure undergoing long-term stable haemodialysis treatment. The patients were tested after a control treatment period of 1 week. Half were fed 30 chitosan tablets (45 mg chitosan/tablet) three times a day. Ingestion of chitosan effectively reduced total serum cholesterol levels (from 10.14+/−4.40 to 5.82+/−2.19 mM) and increased serum haemoglobin levels (from 58.2+/−12.1 to 68+/−9.0 g L-1). During the treatment period, no clinically problematic symptoms were observed. The results suggest that chitosan might be an effective treatment for renal failure patients, although the mechanism of the effect should be investigated further.

Chitosan was also administrated intranasally to deliver morphine in patients following orthopaedic surgery, and was shown to offer a safe and less invasive alternative to intra venous (IV) morphine. An clinical and pharmacokinetic study for a drug delivery system (DDS) of gentamycin-loaded chitosan bar were carried out with the purpose to evaluate its efficacy and giving further data for its clinical applications. Eighteen (18) cases of chronic osteomyelitis were treated by surgical necrectomy with implantation of gentamycin-load chitosan bar in the prepared bone cavity. All of the 18 cases were followed up for 24.8 months (in a range of 6-34 months) 16 patients received initial cure and without any recurrence. So, it could be concluded that the gentamycin-loaded chitosan DDS was a simple and effective method for the treatment of chronic osteomylitis without the necessity to carry out a second operation to remove the drug carrier.

In China, on 12 patients, chitosan was observed to safely prevent or reduce elbow adhesion after elbow arthrolysis. It was investigated again in humans to prevent knee adhesion following patella operation (Kim et al., 2006, Clin. Cancer Res., 12: 543-548; Jing et al., 1997, J Pharm Pharmacol., 49(7): 721-723; Stoker et al., 2008, Pain Med., 9: 3-12; and Chen et al., 1998, Chinese Journal of Reparative and Reconstructive Surgery, 12: 355-358).

Several clinical trials involving chitosan compositions or materials for drug delivery or medical implant purposes are ongoing (recruiting) or terminated in the United States. Chitosan materials are, or have been, clinically studied in patients for the management of difficult spontaneous epistaxis and to evaluate its healing effect on nasal mucosa, to investigate the safety and efficacy of hemostasis of the dressing for use in dental surgical procedures, to test a chitosan pad after diagnostic percutaneous coronary angiography as an adjunct to manual compression to better control vascular access site bleeding and reduce time-to-hemostasis, to investigate a chitosan composition as a safe, effective debridement of chronic wounds in the operating room and inpatient ward settings and to minimize bacterial re-colonization of wounds, to investigate the therapeutic benefits of using a chitosan composition for the wound repair of diabetic neuropathic foot ulcers, to compare the efficacy of a chitosan composition versus conventional treatment in the treatment of Diabetic Neuropathic Foot Ulcer, to investigate a new chitosan derivative for reducing the symptoms associated with Dry Eye Syndroma, and to investigate whether the treatment of damaged cartilage in the knee with a chitosan composition will increase the amount and quality of cartilage repair tissue when compared with microfracture alone. Moreover, chitosan materials are, or have been, clinically studied in patients to determine if chitosan, a short-chained chitosan with a molecular weight of 40 kDa, is safe and effective in lowering LDL-cholesterol levels in patients with mild to moderately elevated cholesterol levels (drug), and to compare safety and immunogenicity of two dosage levels of Norwalk VLP Vaccine with chitosan adjuvant/excipients.

It is also disclosed herein the preparation of highly biocompatible thermogelling solutions of chitosan by using naturally occurring glucosamine-6-phosphate in solution or in solid form. Glucosamine-6-phosphate is the intermediate product in the pathway leading to the natural biosynthesis of glucosamine, recognized as the biochemical precursor of all nitrogen-containing sugars (Roseman, 2001, J. Biol. Chem., 276: 41527-41542), which are important constituents of glycoproteins and oligosaccharides involved in biological recognition. Specifically, glucosamine-6-phosphate is synthesized from fructose-6-phosphate and glutamine (Ghosh et al., 1960, J. Biol. Chem., 235: 1265-1273) as the first step of hexosamine biosynthesis pathway. The end-product of this pathway is uridine diphosphate N-acethylglucosamine or UDP-GlcNAc, a nucleotide sugar used then for making glycosaminiglycans, proteoglycans and glycolipids.

It is conceived herein that any phosphorylated amino-sugar can be used as described hereinabove. Furthermore, contrary to U.S. Pat. No. 6,344,488, the content of which is incorporated herein by reference, which teaches the use of mono-phosphate of polyols and sugars (phosphorylated polyols and sugars), any person having ordinary skill in the art will make the distinction that the present disclosure is directed to the use of amino-sugars which is different from sugars and/or polyols.

Sugar refers to a number of carbohydrates, such as monosaccharides, disaccharides, or oligosaccharides. Monosaccharides are also called "simple sugars," having the formula $C_nH_{2n}O_n$, where n is between 3 and 7. Glucose, which has the molecular formula $C_6H_{12}O_6$, is the most important monosaccharide. The carbohydrates are really just polyhydroxyaldehydes, called aldoses, or polyhydroxyketones, called ketoses, while polyols are simply alcohols containing multiple hydroxyl groups. Chitosan compositions described in the art, such as in U.S. Pat. No. 6,344,488, encompassed sugars being monosaccharide such as mono-phosphate dibasic sugars, mono-sulfate sugars and mono-carboxylic sugars.

An amino-sugar as encompassed herein is a sugar where a hydroxyl group is substituted with an amine group. Derivatives of amine-containing sugars, such as N-acetylglucosamine, while not formally containing an amine, are also considered amino-sugars.

Phosphorylation is the chemical addition of a phosphate ($PO_4$) group to a protein, sugar or other organic molecule. As used herein, glucosamine-6-phosphate refers to glucosamine phosphorylated on carbon 6.

As used herein, "amino-sugar carbonate solution" or "amino-sugar phosphate solution" refers to a solution containing positively charged amino-sugar ($+NH_3$-sugar) among counter-ions needed to balance negatively charged $CO_3^{2-}$ and $PO_4^{3-}$, so that the total charge is zero.

As used herein, "phosphorylated amino-sugar solution" refers to a solution where the negatively charged ion is the amino-sugar-phosphate (amino-sugar-O—$PO_3^{2-}$).

The term "gelating temperature" is intended to mean any temperature ranging from about 25° C. to about 70° C., preferably between 37° C. to about 60° C., and more preferably at about the physiological temperature or 37° C.

The expression "in situ gelation" refers herein to the formation of gels following injection of the liquid chitosan solution as taught herein within specific sites of mammalian or human environments, e.g. any tissues (muscles, bone, ligaments, cartilages) and organs. Gelation in situ allows complete and precise filling of tissue defects or body cavities. The gelation of the chitosan mixture is induced by the physiological temperature.

A chitosan gel as taught herein is an ideal material for drug delivery system. Such an in situ gel-like forming vehicle, wherein a solid particulate or water-soluble additive is incorporated prior to the gelation, can be administrated topically, directly to the body site to be treated or diagnosed. Anti-bacterial, antifungal, steroidal or non-steroidal anti-inflammatory, anti-cancer, anti-fibrosis, anti-viral, anti-glucoma, miotic and anti-cholinergies, anti-psychotic, antihistaminic and decongestant, anesthesic and anti-parasitic agents may be incorporated within the composition and gel. In a similar fashion, polypeptides or non-living pharmaceutical agents may be incorporated within the composition or gel for restorative, reconstructive or regenerative purposes.

The present disclosure will be more readily understood by referring to the following examples which are given to illustrate embodiments rather than to limit its scope.

EXAMPLE I

Preparation of a Mixture of Chitosan-Buffering Solution

1. Preparation of Chitosan Solution

Chitosan solution (2.00% w/v) was prepared by dissolving medical grade chitosan, having medium molecular weight, in aqueous solution of HCl. The ratio of HCl compared to the chitosan amino group ($NH_2$), referred as the degree of protonation of chitosan in solution, was maintained at 70%. The solution was sterilized using an autoclave for 30 minutes at 121° C. After cooling, the water lost caused by the autoclave process was compensated by adding sterile water under controlled aseptic environment. The solution was then aseptically filtered through a metal frit, partitioned in 5.0 mL aliquots and stored at 4° C. An extra aliquot of about 3 mL was used to measure the pH of the chitosan solution. The characteristics of 100 mL solutions prepared using chitosan having DDA of about 80% and 98% are summarized in Table 1.

TABLE 1

Characteristics of chitosan solution (100 mL)

| Chitosan DDA (%) | m (g) | $H_2O$ (mL) | HCl, 1M (mL) | pH |
|---|---|---|---|---|
| 80 | 2.0566 | 93.20 | 6.80 | 5.51 |
| 98 | 2.0586 | 91.26 | 8.74 | 5.50 |

2. Preparation of Buffering Solutions

Buffering solution of glucosamine-carbonate was obtained by co-dissolving simultaneously glucosamine hydrochloride and sodium carbonate in water, while the buffering solution of glucosamine phosphate was prepared by dissolving simultaneously glucosamine hydrochloride and tribasic potassium phosphate. The amounts of salt used for the preparation of 50 mL of each buffering solution are summarized in Table 2. Generally, the pH of the buffering solution is maintained between 7.60 and 8.00 for glucosamine carbonate and between 8.10 and 8.50 for glucosamine phosphate.

For long-term stability, the buffering solutions of glucosamine carbonate and glucosamine phosphate should be stored at very low temperature, below −20° C., preferentially −80° C. This can prevent or stop a probable Maillard reaction-like, which has been suspected to be causing the degradation, revealed by the browning coloration, of the buffering solutions when stored at temperatures above 0° C. Technically, to solve this problem, the buffering solutions glucosamine carbonate and glucosamine phosphate can be prepared at the time of use by mixing a volume of doubly concentrated solution of glucosamine-chloride with a same volume of doubly concentrated solution of carbonate salts or by mixing a volume of doubly concentrated solution of glucosamine with a same volume of doubly concentrated solution of phosphate salts, respectively. These solutions, namely, glucosamine-chloride solution, carbonate solution or phosphate solution, prepared separately, can be stored at 4° C. for at least more than 6 months. At this temperature, degradation does not occur in acidic aqueous solutions of glucosamine hydrochloride, while aqueous solutions of carbonate or phosphate salts are pretty stable.

TABLE 2

| | Buffering solution (50 mL) | |
|---|---|---|
| Components | Glucosamine carbonate | Glucosamine phosphate |
| Glucosamine-HCl (g) | 8.9808 | 8.9858 |
| Na$_2$CO$_3$ (g) | 2.9704 | — |
| K$_3$PO$_4$ (g) | — | 5.3562 |
| pH | 7.68 | 8.39 |

Amounts of salt used for buffering solution

3. Preparation of Thermogelling Solutions Using Glucosamine Carbonate

I. Chitosan DDA=80%

The thermogelling solution was prepared by vigorously mixing 5.00 mL of chitosan solution with 0.56 mL of glucosamine carbonate buffering solution, while maintaining the temperature around 15° C. The resulting solution having a pH of about 6.82 was then poured in a test tube and incubated at 37° C., where it gelled within approximately 10 minutes.

In a second experiment, 5.00 mL of chitosan solution was mixed under vigorous stirring with 0.50 mL of glucosamine-cabonate solution, while maintaining the temperature around 15° C. The resulting solution having a pH value of about 6.75, gelled within 20 minutes at 45° C.

II. Chitosan DDA=98%

The thermogelling solution was prepared by vigorously mixing 5.00 mL of chitosan solution with 0.50 mL of glucosamine carbonate buffering solution, while maintaining the temperature around 15° C. The resulting solution having a pH of about 6.8 was then poured in a test tube and incubated at 37° C., where it gelled within approximately 1 minute.

In a second experiment, 5.0 mL of chitosan solution was mixed under vigorous stirring with 0.40 mL of glucosamine-cabonate solution, while maintaining the temperature around 15° C. The resulting solution having a pH value of about 6.7, gelled within 20 minutes at 45° C. The temperature dependence of elastic modulus (G') and viscous modulus (G") of the latter solution is shown in FIG. 1.

4. Preparation of Thermogelling Solutions Using Glucosamine Phosphate

I. Chitosan DDA=80%

The thermogelling solution was prepared by mixing, under vigorous stirring, 5.00 mL of chitosan solution with 0.60 mL of glucosamine phosphate solution, while maintaining the temperature around 15° C. The resulting solution having a pH of about 7.02 was then poured in a test tube and incubated at 37° C., where it gelled within about 7 minutes.

In a second experiment, 5.00 mL of chitosan solution was mixed under vigorous stirring with 0.50 mL of glucosamine phosphate solution, while maintaining the temperature around 15° C. The resulting solution having a pH value of about 6.81, gelled within 30 minutes at 45° C.

However, thermogelling composition disclosed herein cannot be obtained nor by using glucosamine hydrochloride solution nor by using free glucosamine solution. As the pH of 3.11 measured for a 0.55M glucosamine hydrochloride solution is much lower than that of chitosan solution, the pH of the mixture does not exceed a value of 5.50. Such mixtures remain liquid in the whole range of temperature, from 0 to 80° C. In contrast the use of free glucosamine solution, with pH of 7.71 and 8.03, increases the pH of the mixture, but a substantial precipitation of chitosan occurred as soon as a pH value between 6.2 and 6.4 was reached.

Also, a solution of Na$_2$CO$_3$ cannot be used to prepare the thermogelling composition disclosed herein. When added to chitosan solution, the relatively strong alkalinity of such a carbonate solution (0.373M), pH about 11.5, causes instantaneous precipitation of chitosan. Then acids, including but not limited to organic acids such as glutamic acid and pyruvic acid have been used to soften the alkalinity of carbonate solution and thus provide buffering solution for thermogelling composition disclosed herein. However, these buffering solutions have been found to be less effective than glucosamine carbonate and buffering solution. Table 3 shows the amounts needed for the preparation of glutamic-carbonate solutions with pH values of 7.65 and 7.85. The compositions resulting from the mixing of 5.00 mL of chitosan solution (DDA=98%) with 0.50 mL of solution 1, and with 0.50 mL of solution 2, had respectively a pH value of 6.31 and 6.56.

TABLE 3

Amounts needed for the preparation of glutamic-carbonate solutions

| Glutamic-carbonate (50 mL) | Glutamic acid (g) | Na$_2$CO$_3$ (g) | pH |
|---|---|---|---|
| Solution 1 | 4.5675 | 3.2875 | 7.65 |
| Solution 2 | 6.6525 | 4.9965 | 7.85 |

EXAMPLE II

Preparation of a Thermogelling Solution of Chitosan Using Glucosamine-6-Phosphate Chitosan solution (~2.0% w/v) was prepared as described above in Example I. The thermogelling solution was prepared by mixing 5.0 mL of refrigerated chitosan solution with 0.5 mL of refrigerated glucosamine-6-phosphate disodium salt solution (1M) in ice bath (~4° C.), and under vigorous stirring. The resulting solution having a pH of about 7.0 was then taken out of the ice bath and placed at 37° C., where it gelled within 15 minutes.

EXAMPLE III

Therapeutic Procedures with Dual Thermogelling Composition

The composition disclosed herein can be used for minimally-invasive therapeutic procedures, particularly on musculo-skeletal tissues such as articular cartilage, fibrocartilage and bone to name only a few of them. The composition described herein is particularly suited for treating articular cartilage injuries, and has been clinically applied in patients suffering articular cartilage defects. This composition has been applied by orthopaedic specialists, under a clinical protocol and under the Special Access Program (SAP) from Health Canada, to treat articular cartilage defects in knee joints of patients suffering knee cartilage injuries, knee joint pain and reduced joint functionalities.

A total of 9 patients, aged from 18 to 70 year old, had intact knee ligament structures and suffered from one-compartment symptomatic cartilage lesions, with the cartilage lesions being investigated by the magnetic resonance imaging (MRI), have been treated in Canada. All patients were treated arthroscopically with the debridement of the non-adherent articular cartilage and the composition was administered arthroscopically to fill and cover the cartilage defects. The cartilage defects treated with the composition were up to 3 cm×3 cm in surface area. The composition acts primarily to fill articular cartilage defects and resurfaces the injured cartilage surfaces in the joint. The composition administered in patient' knees has proven to be safe, non-toxic, and easy to prepare and to administer. With a follow-up of 8 to 9 months post-op, all patients treated with the composition showed clear positive clinical outcomes beginning at 3 to 6 months post-op., such positive clinical outcomes consisting primarily in significantly reduced knee joint pain and in improved knee joint functionality and overall patient activity level. Clinical evaluation was performed using WOMAC type scoring and questionnaire. The composition proposed for treating articular cartilage injuries can be used for treating cartilage defects in body joints for knee and other joints, especially in the hip and ankle.

The treatment with the composition described herein is performed during the course of a knee arthroscopy. It is done along with a wash and debridement, and can be associated with a bone marrow stimulating technique (microfracture). The composition can be applied directly onto the Articular Cartilage Injury.

The composition described herein is prepared easily and rapidly during the course of a knee arthroscopy procedure. Furthermore, since it can be administered as an injectable, it is advantageously very easily administered through an arthroscopy and it does not significantly lengthen the duration of arthroscopic procedures.

The treatment of Articular Cartilage Injury with the composition described herein reduced knee joint pain and improved knee joint functions, thus providing enhanced joint functionalities and overall activity level to the treated patients. These beneficial effects should occur as soon as at 3 months post-arthroscopy. This treatment can postpone more aggressive and costly prosthetic treatments of Articular Cartilage Injury.

While the description has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth, and as follows in the scope of the appended claims.

What is claimed is:

1. A method of treating, repairing, regenerating, replacing or substituting a tissue or organ within a mammalian or human body comprising the step of administering a thermogelling composition comprising:
    a) a chitosan solution; and
    b) a buffering solution consisting of an amino-sugar carbonate solution, an amino-sugar phosphate solution or a phosphorylated amino-sugar solution;
wherein the composition, being liquid at a pH between 6.5 and 7.6, is biocompatible, isotonic and turns into gel when heated up to a temperature range between about 25° C. and about 60° C., and cooled down to a temperature range between about 8° C. and about 1° C.

2. The method of claim 1, wherein said buffering solution is a glucosamine carbonate solution, a glucosamine phosphate solution or a glucosamine-6-phosphate solution.

3. The method of claim 1, wherein the composition is injected then gelled in the mammalian or human body.

4. The method of claim 1, wherein said composition is pregelled before being injected in mammalian or human body.

5. The method of claim 1, wherein the tissue or organ comprises articular cartilage, fibrocartilage, meniscus, intervertebral discs, bone tissues, muscular tissues, nerve and spinal cord soft-tissues, skin or dermal tissues.

6. The method of claim 1, wherein the composition is injected intrartricular to treat or improve body joint functions, or to repair cartilage defects.

7. The method of claim 1, wherein said composition is prepared by:
    a) dissolving chitosan in an acidic solution to obtain the aqueous solution of chitosan; and
    b) admixing the buffering solution to said chitosan solution.

8. The method of claim 7, wherein the chitosan is dissolved at a temperature between 15 and 22° C.

9. The method of claim 1, wherein said composition is in liquid state having a pH between 6.7 and 7.2.

10. The method of claim 1, wherein said composition forms a gel when heated up to 37° C.

11. The method of claim 1, wherein the concentration of chitosan ranges from 0.1% to 5.0%.

12. The method of claim 2, wherein the concentration of glucosamine carbonate, glucosamine phosphate or glucosamine-6-phosphate ranges from 0.002M to 0.100M.

13. The method of claim 1, wherein the concentration of chitosan ranges from 1.0% to about 3.0%.

14. The method of claim 2, wherein the ratio of chitosan to glucosamine carbonate, glucosamine phosphate or glucosamine-6-phosphate is between 1 and 3.

15. The method of claim 1, wherein said chitosan has a degree of deacetylation (DDA) ranging between 70% and 100% and a molecular weight (Mw) ranging from 50 kDa to 1000 kDa.

16. The method of claim 1, wherein said chitosan has a degree of deacetylation (DDA) of 80% to 99%, and a Mw of 200 kDa to 500 kDa.

17. The method of claim 1, wherein the osmolarity of said composition is between 270 mOsmol/kg and 340 mOsmol/kg.

18. The method of claim 1, further comprising at least one material or compound selected from the group consisting of cells, stem cells, peptides, growth factors, human blood, platelet-rich plasma, nucleotides, bone, bone-derived materials, calcium phosphates, calcium carbonates, bioglasses, ceramics, drugs and imaging agents.

19. The method of claim 18, wherein said calcium phosphate particles are biphasic calcium phosphates, tetra-calcium phosphates, tri-calcium phosphates, hydroxyapatite, di-calcium phosphates, mono-calcium phosphates, amorphous calcium phosphates, octa-calcium phosphate, fluorinated calcium phosphate, strontied calcium phosphate, or a mixture thereof.

* * * * *